United States Patent [19]

Drell

[11] Patent Number: 5,389,617
[45] Date of Patent: Feb. 14, 1995

[54] METHOD FOR ADMINISTRATION OF AZAURIDINE AND PYRIDOXINE FOR THE TREATMENT OF RHEUMATOID ARTHRITIS

[75] Inventor: William Drell, San Diego, Calif.

[73] Assignee: UR Labs, Inc., San Diego, Calif.

[21] Appl. No.: 152,255

[22] Filed: Nov. 12, 1993

Related U.S. Application Data

[63] Continuation of Ser. No. 822,630, Jan. 17, 1992, abandoned.

[51] Int. Cl.$^6$ ............... A61K 31/70; A61K 31/44
[52] U.S. Cl. .................................. 514/43; 514/332; 514/825; 514/922
[58] Field of Search ............ 514/43, 332, 825, 922

[56] References Cited

PUBLICATIONS

New Indications For 6-Azauridine Treatment In Man, by Elis and Raskova, Europ.J.Clin.Pharmacol. 4, 77–81 (1972).

Side Effects Of 67-Azauridine Triacetate In Rheumatoid Arthritis, by Elis, Slavik, Raskova, Clin.Pharmacol. & Therap., II., 404–407 (1970).

Unexpected Side Effects of 6-Azauridine In Rheumatoid Arthritis And Feedback In Animal Experiments, by Raskova, Elis, Perlik, Polansky and Slavik, Proc.-Soc.Europ. for the Study of Drug Toxicity, Upsala, Jun. 1970, 12 191 (1971).

Chemical Abstracts 74:109871p (1971).
Chemical Abstracts 77:14345t (1977).

*Primary Examiner*—Raymond J. Henley, III
*Assistant Examiner*—K. Weddington
*Attorney, Agent, or Firm*—Christie, Parker & Hale

[57] ABSTRACT

A method for treating patients with rheumatoid arthritis comprises administering azaribine to the patient at a dosage level of 10 to 50 mg/kg/day for an initial period of from about 1 to about 3 weeks and then administering azaribine to the patient at dosage levels of at least 50 mg/kg/day and preferably at least 100 mg/kg/day.

12 Claims, No Drawings

METHOD FOR ADMINISTRATION OF AZAURIDINE AND PYRIDOXINE FOR THE TREATMENT OF RHEUMATOID ARTHRITIS

CROSS-REFERENCE TO RELATED APPLICATION

This is a continuation of application Ser. No. 07/822,630, filed Jan. 1992, now abandoned.

FIELD OF THE INVENTION

This invention relates to the treatment of rheumatoid arthritis and more particularly to a method for administering, 6-azauridine, azaribine or other 6-azauridine compound for treating rheumatoid arthritis.

BACKGROUND OF THE INVENTION

Azaribine (2', 3', 5'-triacetyl-6-azauridine) has been found to be effective in oral dosage form for the treatment of psoriasis, psoriatic arthritis, mycosis fungoides, herpes simplex, and small pox. Typical dosage levels for the treatment of such conditions are 125 to 250 mg/kg/day. It has been found that such a dosage level may be given for many weeks without side effects, particularly when administered in combination with pyridoxine or other pyridoxine compound, such as pyridoxal phosphate.

At high doses, azaribine demonstrates anti-inflammatory properties. For this reason, azaribine has been tested for the treatment of rheumatoid arthritis. However, at dosage levels of azaribine of 100 mg/kg/day or higher given to patents with rheumatoid arthritis, severe side effects have been reported including fever, joint pain, joint swelling, edema, nausea, emesis, exanthema, painful and rigid muscles and depression. Elis and Raskova, "New Indications for 6-Azauridine Treatment in Man, A Review," Europ.J.Clin. Pharmacol. 4, 77–81 (1972); Elis, Slavik, Ruskova, "Side Effects of 6-Azauridine triacetate in Rheumatoid Arthritis," Clin. Pharmacol. & Therap., II., 404–407 (1970) It has further been reported that slight side effects were produced even at dosage levels of 50 mg/kg per day. Ruskova, Elis, Perlik, Polansky and Slavik, "Unexpected Side Effects of 6-Azauridine in Rheumatoid Arthritis and Feedback in Animal Experiments," Proc. Soc. Europ for the Study of Drug Toxicity," Upsala: June 1970, 12 191 (1971). It is believed that for this reason, no work has been done on this indication for the last 20 years.

SUMMARY OF THE INVENTION

The present invention provides a method for treating patients with rheumatoid arthritis. The method comprises administering an azauridine compound, preferably azaribine, to the patient at a dosage level of from about 10 to about 50 mg/kg/day and preferably from about 15 to about 35 mg/kg/day for a predetermined period, preferably from about 1 to about 3 or 4 weeks. This is followed by the administration of azaribine at dosage levels of at least about 50 and preferably at 100 mg/kg/day or higher for as long as the patient shows improvement.

It is preferred that the azauridine compound be administered as azaribine so that it can be administered orally. It is further preferred that the azaribine be administered in a formulation which is resistant to absorption by the stomach. A preferred chemical formulation comprises a generally solid composition containing azaribine which is then encapsulated in an enteric coating. The formulation may be orally administered in tablet, capsule or other suitable form. It is understood that other methods of administrations such as oral administration of non-enteric coated azaribine or intravenous administration of 6-azauridine, may be used as desired.

In a preferred embodiment of the invention, the method further comprises the administration of a pyridoxal phosphate compound, preferably pyridoxine as the HCl salt, which is administered within twenty-four hours before or after oral administration of the azauridine compound and preferably administered simultaneously with the azauridine compound. The pyridoxine compound is administered in an amount sufficient to supply at least 0.0005 mole, preferably at least about a 0.001 mole, and more preferably at least about a 0.025 mole of the pyridoxine compound per mole of the administered azauridine compound.

DETAILED DESCRIPTION

In accordance with the present invention there is provided a method for the administration of azaribine or other azauridine compound for treating patients with rheumatoid arthritis without the adverse side effects previously disclosed.

The method comprises administering an azauridine compound to patients suffering from rheumatoid arthritis in an amount from about 10 to about 50 milligrams per kilogram of patient body weight per day ("mg/kg/day") and preferably from about 15 to about 35 mg/kg/day. The administration of the azauridine compound at such levels is continued for an initial period, preferably of from about one to about three weeks.

If no adverse side effects are noticed, the administration of the azauridine compound is continued at higher dosage levels, preferably at least about 50 mg/kg/day and more preferably at least about 100 mg/kg/day. Administration of the azauridine compound at higher dosage levels is continued as long as the patient shows improvement as marked alleviation of his or her symptoms.

If desired, the method may comprise the administration of one or more intermediate dosage levels of azauridine compound following the initial administration period. For example, the azauridine compound may be administered for one to three weeks at a dosage level from 10 to about 50 mg/kg/day then increased for two to three weeks to a level of 50 to 100 mg/kg/day and then administered at a dosage level of greater than 100 mg/kg/day.

If free azauridine, i.e. 6-azauridine, is used, the administration must be by intravenous infusion. This is because, if administered orally, intestinal bacteria partially metabolizes azauridine into 6-azauracil, which is toxic. Accordingly, it is preferred to use suitable esters of azauridine which may be administered orally. The presently preferred azauridine compound is the triacetate ester azaribine (2', 3', 5'-triacetyl-6-azauridine).

The azaribine is preferably administered as a solid composition containing azaribine which had been encapsulated in an enteric coating as described in U.S. Pat. No. 5,023,083 which is incorporated herein by reference.

Administration of azauridine compounds orally typically results in a pyridoxal phosphate deficiency and abnormally high levels of homocystine. While this problem is minimized, if not eliminated, by the use of enteric coatings, it is still preferred that administration of the azauridine compound, be accompanied by the administration of a pyridoxine compound selected from the group consisting of pyridoxine, pyridoxal phosphate, pyridoxamine, pyridoxamine phosphate, pyridoxal, pyridoxine phosphate and mixtures thereof. The pyridoxine compound is preferably administered within twenty-four hours before or after the administration of the azauridine compound and preferably simultaneously with the azauridine compound. The pyridoxine compound is administered in an amount sufficient to supply at least 0.0005 mole, preferably at least about 0.001 mole and more preferably at least about 0.025 mole of the pyridoxine compound per mole of the administered azauridine compound. The presently preferred pyridoxine compound is pyridoxine hydrochloride.

While the reasons are not fully understood, it has been found that the adverse side effects in rheumatoid arthritis patients which generally accompany the administration of azaribine in dosage levels above 50 mg/kg/day can be mitigated and even eliminated, in most patients, by administering the azaribine in low dosage levels during an initial period which is then followed by the administration of azaribine at elevated levels, i.e. above 50 mg/kg/day. The administration of azaribine in such a schedule has been shown to reduce the erthrocyte sedimentation rate, improve the joint tenderness/pain index, the joint/swelling index and the feeling of well being of patients suffering from rheumatoid arthritis.

What is claimed is:

1. A method for treating rheumatoid arthritis in a patient comprising:
   (a) administering to the patient an azauridine compound in an amount of from about 10 to about 50 mg/kg/day, and a pyridoxine compound in an amount of at least 0.0005 mole per mole of azauridine, for an initial period sufficient to reduce the adverse side effects associated with the administration of azauridine compounds at dosage levels of at least 50 mg/kg/day during subsequent administration of an azauridine compound at a higher dosage level of at least 50 mg/kg/day; and then
   (b) administering to the patient an azauridine compound at a higher dosage level of at least about 50 mg/kg/day, and a pyridoxine compound in an amount of at least 0.0005 mole per mole of azauridine, for a second period sufficient to show improvement in the rheumatoid arthritis.

2. A method as claimed in claim 1 wherein the initial period is from about one to about four weeks.

3. A method is claimed in claim 1 wherein, after the second period, an azauridine compound is administered at a dosage level of at least 100 mg/kg/day for as long as the patient shows improvement.

4. A method as claimed in claim 3 wherein the second period is from about four weeks to about eight weeks.

5. A method as claimed in claim 1 wherein the azauridine compound is administered at dosage levels of from about 15 to about 35 mg/kg/day during the initial period.

6. A method as claimed in claim 1 wherein the azauridine compound is administered in an amount of at least about 100 mg/kg/day during the second period.

7. A method as claimed in claim 1 wherein the azauridine compound is azaribine.

8. A method as claimed in claim 7 wherein the azaribine is administered orally.

9. A method as claimed in claim 8 wherein the azaribine compound is encapsulated in an enteric coating.

10. A method as claimed in claim 1 wherein the azauridine compound is 6-azauridine.

11. A method as claimed in claim 10 wherein the 6-azauridine is administered by intravenous infusion.

12. A method for treating rheumatoid arthritis in a patient comprising:
   administering to the patient an azauridine compound in an amount of from about 10 to about 50 mg/kg/day, and a pyridoxine compound in an amount of at least 0.0005 mole per mole of azauridine, for a period of from about 1 to about 4 weeks; and then
   administering to the patient an azauridine compound in an increased amount of from about 50 to about 100 mg/kg/day, and a pyridoxine compound in an amount of at least 0.0005 mole per mole of azauridine, for a second period of from about 4 to about 8 weeks; and then
   administering to the patient an azauridine compound in a further increased amount of at least about 100 mg/kg/day, and a pyridoxine compound in an amount of at least 0.0005 mole per mole of azauridine, for a third period for as long as the patient shows improvement.

* * * * *

UNITED STATES PATENT AND TRADEMARK OFFICE
CERTIFICATE OF CORRECTION

PATENT NO. : 5,389,617
DATED : February 14, 1995
INVENTOR(S) : William Drell

It is certified that error appears in the above-indentified patent and that said Letters Patent is hereby corrected as shown below:

Column 1, line 9, change "Jan. 1992" to
-- Jan. 17, 1992 --.

Column 1, line 40, "(1970)" insert a period.

Signed and Sealed this

Nineteenth Day of September, 1995

Attest:

BRUCE LEHMAN

*Attesting Officer*     *Commissioner of Patents and Trademarks*